(12) United States Patent
Yao et al.

(10) Patent No.: US 12,012,430 B2
(45) Date of Patent: Jun. 18, 2024

(54) METHOD FOR PREPARING LIQUID MALTITOL AND LIQUID POLYOLS FROM A RAFFINATE INCLUDING MALTITOL

(71) Applicant: ZHEJIANG HUAKANG PHARMACEUTICAL CO., LTD., Zhejiang (CN)

(72) Inventors: Yanhui Yao, Quzhou (CN); Xinfeng Han, Quzhou (CN); Fuan Wan, Quzhou (CN); Hang Yue, Quzhou (CN); Weixing Shen, Quzhou (CN); Haojun Dai, Quzhou (CN); Mingqian Yang, Quzhou (CN); Mian Li, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

(21) Appl. No.: 18/469,518

(22) Filed: Sep. 18, 2023

(65) Prior Publication Data
US 2024/0010667 A1    Jan. 11, 2024

Related U.S. Application Data

(63) Continuation of application No. PCT/CN2022/133110, filed on Nov. 21, 2022.

(30) Foreign Application Priority Data

Dec. 23, 2021 (CN) .......................... 202111588188.2

(51) Int. Cl.
  *C07H 15/04*  (2006.01)
(52) U.S. Cl.
  CPC .................................. *C07H 15/04* (2013.01)
(58) Field of Classification Search
  CPC .................................................... C07H 15/04
  See application file for complete search history.

(56) References Cited

U.S. PATENT DOCUMENTS

| 2002/0055150 A1* | 5/2002 | Caboche ................ C12P 19/22 435/95 |
| 2017/0320800 A1 | 11/2017 | Smith et al. |
| 2022/0411839 A1 | 12/2022 | Mao et al. |

FOREIGN PATENT DOCUMENTS

| CN | 105085583 A | 11/2015 |
| CN | 104177229 B | 2/2016 |
| CN | 109734756 A | 5/2019 |
| CN | 112266319 A | 1/2021 |
| CN | 112704221 A | 4/2021 |
| CN | 114249780 A | 3/2022 |

OTHER PUBLICATIONS

International Search Report in PCT/CN2022/133110 dated Feb. 11, 2023, 5 pages.

* cited by examiner

*Primary Examiner* — Bahar Craigo
(74) *Attorney, Agent, or Firm* — METIS IP LLC

(57) ABSTRACT

The present disclosure relates to a method for preparing liquid maltitol and liquid polyols from a raffinate including maltitol. The method comprises the following steps: obtaining a hydrogenated liquid by hydrogenating a pre-treated raffinate including maltitol, obtaining a post-treated liquid by post-treatment of the hydrogenated liquid to remove impurities, obtaining a dilute liquid and a concentrated maltitol solution by membrane-separation of the post-treated liquid, and using the dilute liquid as the liquid polyols, and obtaining the liquid maltitol by mixing the concentrated maltitol solution with a prepared maltitol solution with a maltitol content of over 50%, wherein the liquid maltitol has a maltitol content greater than or equal to 50% and meets a standard. Before the membrane separation process, the present disclosure reduces the reducing sugar content in the liquid by hydrogenation to lower the risk of yellowing during the process and to improve the quality of the final product.

5 Claims, 1 Drawing Sheet

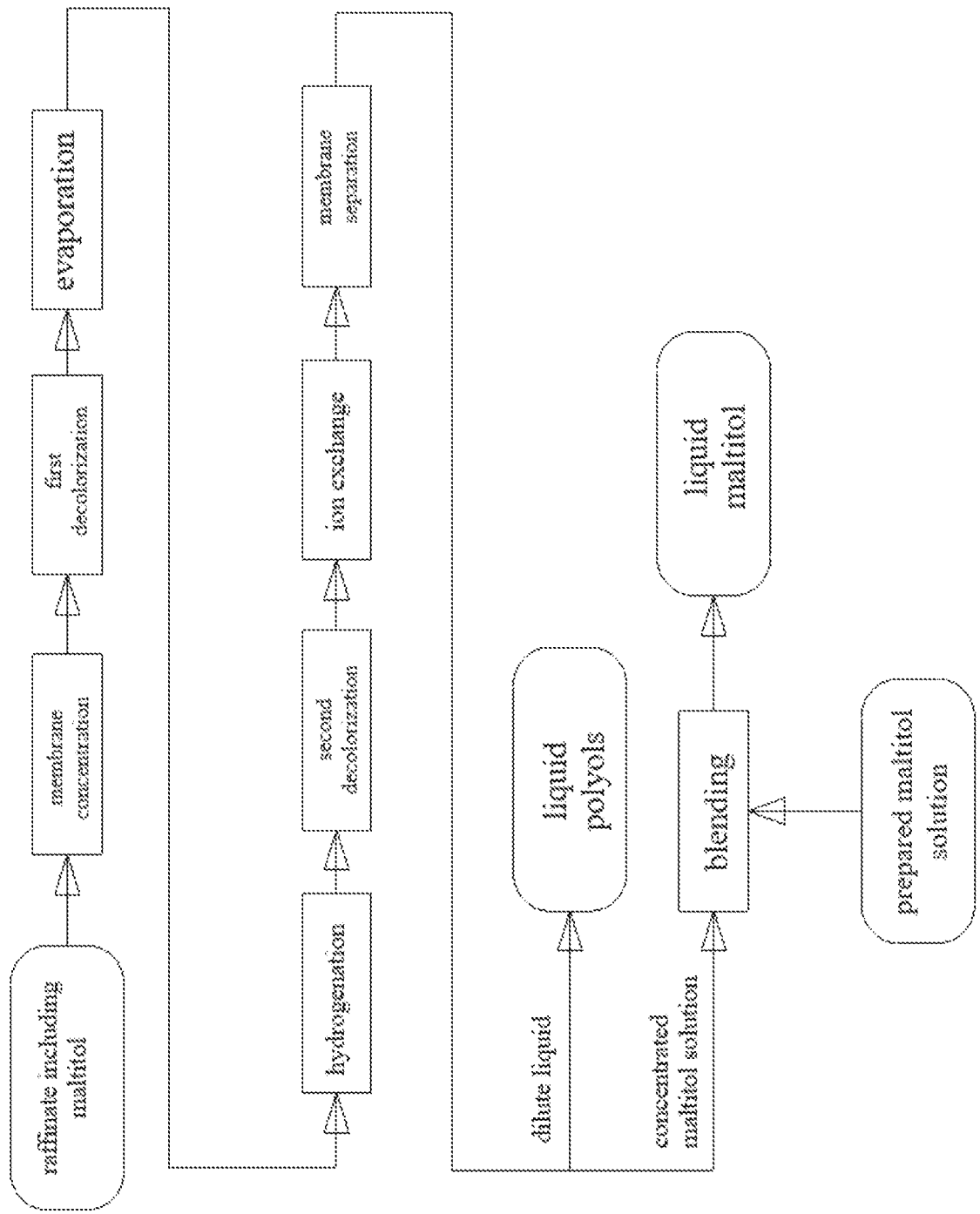

METHOD FOR PREPARING LIQUID MALTITOL AND LIQUID POLYOLS FROM A RAFFINATE INCLUDING MALTITOL

CROSS-REFERENCE TO RELATED APPLICATIONS

This application is a continuation of International Application No. PCT/CN2022/133110 filed on Nov. 21, 2022, which claims priority to Chinese Patent Application No. 202111588188.2 filed on Dec. 23, 2021, the entire contents of which are incorporated herein by reference.

TECHNICAL FIELD

The present disclosure belongs to the field of the recycling of a raffinate including maltitol, and more particularly, relates to a method for preparing liquid maltitol and liquid polyols using a raffinate including maltitol.

BACKGROUND

Crystal maltitol is obtained through processes such as decolorization, chromatography, and crystallization on crude maltitol liquid, which is obtained by hydrogenating a high-quality maltose syrup (maltose content ≥85%) obtained by enzymatic liquefaction and saccharification of high-quality starch as raw material. The raffinate which includes maltitol obtained after chromatographic separation of the crude maltitol liquid has main components including maltitol (15%~40%), sorbitol (25%~40%), and oligosaccharide alcohols (35%~45%), usually used as liquid polyol products with low added value. If some of the maltitol components can be separated from the raffinate and used to produce liquid maltitol, the added value of the raffinate can be increased.

Patent CN104177229B discloses a process for preparing solid oligosaccharide alcohols and solid sorbitol from a raffinate, giving high added value of the raffinate. However, this method uses chromatographic separation technology to obtain three different types of raffinate, and the component rich in maltitol is returned to the system, while the raffinates rich in oligosaccharide alcohols and sorbitol are respectively subjected to crystallization and purification. The method is complex and difficult to operate.

Patent CN111206056A discloses a method for preparing sorbitol liquid and liquid polyols using raffinate including maltitol. By adding glucose saccharifying enzymes and dry yeast in the raffinate for fermentation, and the sorbitol liquid and liquid polyols is obtained by decolorization, filtration, and membrane separation to the fermentation liquid. This method reduces the content of reducing sugars and oligosaccharides and increases the sorbitol content through fermentation with saccharifying enzymes, but the saccharification and fermentation time are long, which affects the efficiency.

SUMMARY

The technical problem solved by the present disclosure is to provide a method for preparing liquid maltitol and liquid polyols from a raffinate including maltitol. The method involves hydrogenating the raffinate including maltitol to reduce the content of reducing sugar in the raffinate, and then using membrane separation to obtain liquid polyols and concentrated maltitol solution, separately. The concentrated maltitol solution is then mixed with a pre-existing high-content maltitol solution to obtain a liquid maltitol that meets a national standard. This method effectively utilizes the raffinate which includes maltitol, improves its added value, and is simple and cost-effective. The method of the present disclosure is simple to operate, has a short production cycle, and achieves comprehensive utilization of by-products, resulting in good economic benefits.

Specifically, the method includes the following steps: obtaining a hydrogenated liquid by hydrogenating a pre-treated raffinate including maltitol; obtaining a post-treated liquid by post-treatment of the hydrogenated liquid to remove impurities; obtaining a dilute liquid and a concentrated maltitol solution by membrane-separation of the post-treated liquid; and using the dilute liquid as the liquid polyols, and obtaining the liquid maltitol by mixing the concentrated maltitol solution with a prepared maltitol solution with a maltitol content of over 50%, wherein the liquid maltitol has a maltitol content greater than or equal to 50% and meets a standard.

The pre-treated raffinate has a refractive index of 48%-54%, a maltitol content of 15%-40%, a sorbitol content of 25%-40%, and an oligosaccharide alcohol content of 35%~45%.

In normal situations, the raffinate including maltitol has a maltitol content of 15%-40%, a sorbitol content of 25%-40%, and an oligosaccharide alcohol content of 35%~45%.

The national standard for liquid maltitol includes that the maltitol content is ≥50%, the sorbitol content is ≤8%, and the reducing sugar content is ≤0.3%. In the obtained liquid maltitol of the present disclosure, the maltitol content is in a range of 50.2% to 60%, the sorbitol content is in a range of 1% to 5.7%, and the reducing sugar content is in a range of 0.1% to 0.14%, which fully comply with the national standard for liquid maltitol.

Furthermore, the pretreatment of the raffinate including maltitol includes membrane concentration or evaporation concentration, first decolorization treatment, and evaporation treatment.

Furthermore, an evaporator used in the evaporation treatment includes at least one of a triple-effect evaporator, a quadruple-effect evaporator, a mechanical vapor recompression (MVR) evaporator, and a plate evaporator.

Furthermore, the post-treatment of the hydrogenated liquid includes secondary decolorization treatment and ion exchange treatment.

Furthermore, the pre-treated raffinate including maltitol is hydrogenated at a condition including: a hydrogenation reaction temperature of 130° C.-145° C., pH of a hydrogenation reaction liquid of 5.5-6.5, and a hydrogenation reaction pressure of 6 MPa-8 MPa.

Furthermore, the method comprises the following steps: obtaining a pre-treated solution having a refractive index of 49.5% by pre-treating a raffinate including maltitol, obtaining a hydrogenated liquid by hydrogenating the pre-treated solution, obtaining a post-treated liquid by removing impurities from the hydrogenated liquid through post-treatment, and obtaining a dilute liquid and a concentrated maltitol solution by using a membrane separation device to separate the post-treated liquid, wherein the dilute liquid is used as liquid polyols, and the concentrated maltitol solution is blended with a prepared maltitol solution with a maltitol content greater than 50% in a ratio of 1:0.75 to obtain the liquid maltitol with a maltitol content of 50.2% and a sorbitol content of 4.6%, the liquid maltitol meeting a standard.

Furthermore, the method comprises the following steps: obtaining a pre-treated solution having a refractive index of 49.5% by pre-treating a raffinate including maltitol, obtaining a hydrogenated liquid by hydrogenating the pre-treated solution, obtaining a post-treated liquid by removing impurities from the hydrogenated liquid through post-treatment, and obtaining a dilute liquid and a concentrated maltitol solution by using a membrane separation device to separate the post-treated liquid, wherein the dilute liquid is used as liquid polyols, and the concentrated maltitol solution is blended with a prepared maltitol solution with a maltitol content greater than 50% in a ratio of 1:0.75 to obtain the liquid maltitol with a maltitol content of 50.2% and a sorbitol content of 5.7%, the liquid maltitol meeting a standard.

Compared with existing technologies, the method of preparing liquid maltitol and liquid polyols from a raffinate including maltitol by the present disclosure involves obtaining a hydrogenated liquid by hydrogenating a pre-treated raffinate including maltitol, obtaining a post-treated liquid by post-treatment of the hydrogenated liquid to remove impurities, obtaining a dilute liquid and a concentrated maltitol solution by membrane-separation of the post-treated liquid, and using the dilute liquid as the liquid polyols, and obtaining the liquid maltitol by mixing the concentrated maltitol solution with a prepared maltitol solution with a maltitol content of over 50%, wherein the liquid maltitol has a maltitol content greater than or equal to 50% and meets a standard.

This disclosure uses membrane separation technology to obtain an enriched maltitol solution and a dilute solution of liquid polyols, and by increasing the ratio of the concentrated maltitol solution blending with the prepared maltitol solution, can improve the value of the raffinate including maltitol. In addition, this invention also has the following advantages:

1. Before using membrane separation treatment, the reducing sugar content in the sugar solution through hydrogenation method is reduced, thereby reducing the risk of the product turning yellow in the preparation process and improving the quality of the final product.

2. The operation is simple, the production cycle is short, and by-products are comprehensively utilized, which has good economic benefits.

BRIEF DESCRIPTION OF THE DRAWINGS

FIG. 1 shows a schematic diagram of the process for preparing liquid maltitol and liquid polyols using maltitol chromatography eluent by the present disclosure.

DETAILED DESCRIPTION

In order to make the technical problem, technical solution, and beneficial effects to be solved by the present disclosure more clear and understandable, the following detailed description of the present disclosure will be further explained in conjunction with the drawings and embodiments. It should be understood that the specific embodiments described herein are merely used to explain the present disclosure and are not intended to limit the present disclosure.

As used herein, "liquid" and "solution" can be used interchangeably. For example, hydrogenated liquid is also referred to as hydrogenated solution.

Referring to FIG. 1, the present disclosure provides an embodiment of a method for preparing liquid maltitol and liquid polyols from a raffinate including maltitol. The direction indicated by the arrow in FIG. 1 represents the production flow.

The method includes the following steps: obtaining a hydrogenated liquid by hydrogenating a pre-treated raffinate including maltitol, obtaining a post-treated liquid by post-treatment of the hydrogenated liquid to remove impurities, and obtaining a dilute liquid and a concentrated maltitol solution by membrane-separation of the post-treated liquid. The dilute solution is used directly as a liquid polyol, and the concentrated maltitol solution is mixed with an existing maltitol solution containing more than 50% maltitol, to obtain a liquid maltitol with a maltitol content of ≥50% and in compliance with a national standard.

In some embodiments, the raffinate including maltitol is a liquid from an original material through chromatographic separation. Besides the maltitol, the raffinate also includes sorbitol, oligosaccharide alcohol, etc. After a raffinate including maltitol is pretreated, a pre-treated solution is obtained. The refractive index of the pre-treated solution is 48-54%, and the maltitol content is 15%-40%, the sorbitol content is 25%-40%, and the oligosaccharide alcohol content is 35%-45%.

In some embodiments, the pre-treatment of the raffinate including maltitol includes concentration process (e.g., membrane concentration or evaporation concentration), first decolorization (e.g., using a decolorising agent), and evaporation processes. The post-treatment of the hydrogenation solution includes secondary decolorization (e.g., using a decolorising agent) and ion exchange processes. The post-treatment is used to remove impurities (e.g., catalyst in the reaction, nickel ion. etc.) in the hydrogenated liquid. In the evaporation process, any one of a triple-effect evaporator, a quadruple-effect evaporator, a mechanical vapor recompression (MVR) evaporator, or a plate evaporator can be used.

In some embodiments, the hydrogenation treatment condition is as follows: the hydrogenation reaction temperature is 130° C.-145° C., the pH value of the hydrogenation reaction solution is 5.5-6.5, and the hydrogenation reaction pressure is 6 MPa-8 MPa. In some embodiments, the hydrogenation reaction temperature is 120° C. -160° C., the pH value of the hydrogenation reaction solution is 5.0-6.8, the hydrogenation reaction pressure is 4 MPa-10 MPa. By hydrogenation treatment, the reducing sugar content can be reduced in the hydrogenated liquid, making the final product meet the standard.

In some embodiments, membrane separation includes microfiltration, ultrafiltration, nanofiltration and hyperfiltration.

The content of each sugar alcohol in the dilute solution and concentrated maltitol solution obtained is shown in Table 1.

TABLE 1

Content of each sugar alcohol in dilute and concentrated maltitol solutions

| | Maltitol | Sorbitol | Oligosaccharide alcohol | Reducing Sugar |
|---|---|---|---|---|
| Dilute Solution | 9%~15% | 40%~60% | 15%~25% | 0.10%~0.20% |
| Concentrated Maltitol Solution | 35%~50% | 7%~15% | 36%~48% | 0.05%~0.15% |

The dilute solution meet a standard for liquid polyols, that is, the reducing sugar content is less than 0.3%, which can be used directly as liquid polyols. The concentrated solution is enriched in maltitol and can be mixed with an existing liquid maltitol with a maltitol content of more than 50% to achieve a mixed liquid maltitol that meets a national standard (e.g., GB 28307-2012), that is, a maltitol content ≥50%, a xylitol content ≤8%, and a reducing sugar content ≤0.3%. In the existing liquid maltitol, the maltitol content is 60%, the xylitol content is 3%, and the reducing sugar content is 0.1%.

Below is a further explanation of the method of the present disclosure through specific examples.

EXAMPLE 1

This example is an embodiment of the method for preparing liquid maltitol and liquid polyols using maltitol chromatographic eluate according to the present disclosure. The method includes the following steps:

First, a raffinate including maltitol is pretreated to obtain a pre-treated solution with a refractive index of 49.5%, followed by hydrogenation. The hydrogenation reaction temperature is 137° C., the pH value of the hydrogenation reaction liquid is 5.9, and the hydrogenation reaction pressure is 7 MPa. The conversion rate of hydrogenation is determined to be 99.88%, and the content of reducing sugar in the hydrogenated liquid is determined to be 0.13%.

The hydrogenated liquid is then subjected to decolorization and ion exchange post-treatment to remove impurities, and a dilute liquid and a concentrated maltitol solution are obtained by using a membrane separation device to separate the post-treated liquid. The dilute solution is used as liquid polyols, and the concentrated maltitol solution is mixed with an existing maltitol solution with a maltitol content of more than 50% in a ratio of 1:0.75 to obtain a liquid maltitol that meets a national standard. The obtained liquid maltitol has a maltitol content of 50.2% and a sorbitol content of 5.6%. In some embodiments, the existing/preprepared maltitol solution includes a commercial maltitol solution product. In some embodiments, the existing/preprepared maltitol solution includes a maltitol solution prepared for, e.g., commercial sale.

The content of each sugar alcohol component in the dilute solution, concentrated maltitol solution, and the prepared maltitol solution used for mixing with the concentrated maltitol solution is shown in Table 2.

TABLE 2

Content of each sugar alcohol component in dilute solution, concentrated maltitol solution, and the prepared maltitol solution

|  | Maltitol | Sorbitol | Oligosaccharide alcohol | Reducing Sugar |
|---|---|---|---|---|
| Dilute Solution | 11% | 48% | 19% | 0.15% |
| Concentrated Maltitol Solution | 37% | 9% | 39% | 0.06% |
| Prepared Maltitol Solution | 60% | 3% | / | / |

EXAMPLE 2

This example is an embodiment of the method for preparing liquid maltitol and liquid polyols from a raffinate including maltitol according to the present disclosure.

A raffinate including maltitol is pretreated to obtain a pre-treated solution with a refractive index of 49.5%, and then pre-treated solution is subjected to hydrogenation. The hydrogenation reaction temperature is 136° C., the pH value of the hydrogenation reaction liquid is 6.1, and the hydrogenation reaction pressure is 7.5 MPa. The conversion rate of hydrogenation is determined to be 99.85%, and the content of reducing sugar in the hydrogenated liquid is determined to be 0.14%.

The hydrogenated liquid is then subjected to decolorization and ion exchange treatment to remove impurities, and a dilute liquid and a concentrated maltitol solution are obtained by using a membrane separation device to separate the post-treated liquid, where the dilute solution is used as liquid polyols. The concentrated maltitol solution is blended with a prepared maltitol solution containing more than 50% maltitol in a ratio of 1:1.9 to obtain a liquid maltitol that meets the national standard. The liquid maltitol has a maltitol content of 54.8% and a sorbitol content of 4.7%.

The content of each sugar alcohol component in the dilute solution, concentrated maltitol solution, and the prepared maltitol solution used for mixing with the concentrated maltitol solution is shown in Table 3 below.

TABLE 3

Content of each sugar alcohol component in the dilute solution, concentrated maltitol solution, and the prepared maltitol solution

|  | Maltitol | Sorbitol | Oligosaccharide alcohol | Reducing Sugar |
|---|---|---|---|---|
| Dilute Solution | 15% | 45% | 20% | 0.17% |
| Concentrated Maltitol Solution | 45% | 8% | 40% | 0.07% |
| Prepared Maltitol Solution | 60% | 3% | / | / |

The above description is only the preferred embodiments of the present disclosure, and should not be used to limit the present disclosure. Any modifications, equivalent substitutions, and improvements made within the spirit and principle of the present disclosure should be included within the scope of protection of the present disclosure.

What is claimed is:

1. A method for preparing liquid maltitol and liquid polyols from a raffinate including maltitol, comprising:
   obtaining a hydrogenated liquid by hydrogenating a pre-treated raffinate including maltitol, the pre-treated raffinate having a refractive index of 48%-54%, a maltitol content of 15%-40%, a sorbitol content of 25%-40%, and an oligosaccharide alcohol content of 35%~45%;
   obtaining a post-treated liquid by post-treatment of the hydrogenated liquid to remove impurities;
   obtaining a dilute liquid and a concentrated maltitol solution by membrane-separation of the post-treated liquid; and
   using the dilute liquid as the liquid polyols, and obtaining the liquid maltitol by mixing the concentrated maltitol solution with a prepared maltitol solution with a maltitol content of over 50%, wherein the liquid maltitol has a maltitol content greater than or equal to 50%, wherein the pre-treatment of the raffinate including maltitol includes membrane concentration or evaporative concentration, first decolorization treatment, and evaporation treatment, and the post-treatment of the hydrogenated liquid includes secondary decolorization treatment and ion exchange treatment.

2. The method according to claim 1, wherein an evaporator used in the evaporation treatment includes at least one of a triple-effect evaporator, a quadruple-effect evaporator, a mechanical vapor recompression (MVR) evaporator, and a plate evaporator.

3. The method according to claim 1, wherein the pre-treated raffinate including maltitol is hydrogenated at a condition including: a hydrogenation reaction temperature of 130° C.-145° C., pH of a hydrogenation reaction liquid of 5.5-6.5, and a hydrogenation reaction pressure of 6 MPa-8 MPa.

4. The method according to claim 1, comprising:
obtaining a pre-treated solution having a refractive index of 49.5% by pre-treating the raffinate including maltitol,
obtaining a hydrogenated liquid by hydrogenating the pre-treated solution,
obtaining a post-treated liquid by removing impurities from the hydrogenated liquid through post-treatment, and
obtaining a dilute liquid and a concentrated maltitol solution by using a membrane separation device to separate the post-treated liquid, wherein the dilute liquid is used as liquid polyols, and the concentrated maltitol solution is blended with a prepared maltitol solution with a maltitol content greater than 50% in a ratio of 1:0.75 to obtain the liquid maltitol with a maltitol content of 50.2% and a sorbitol content of 4.6%.

5. The method according to claim 1, comprising:
obtaining a pre-treated solution having a refractive index of 49.5% by pre-treating the raffinate including maltitol,
obtaining a hydrogenated liquid by hydrogenating the pre-treated solution,
obtaining a post-treated liquid by removing impurities from the hydrogenated liquid through post-treatment, and
obtaining a dilute liquid and a concentrated maltitol solution by using a membrane separation device to separate the post-treated liquid, wherein the dilute liquid is used as liquid polyols, and the concentrated maltitol solution is blended with a prepared maltitol solution with a maltitol content greater than 50% in a ratio of 1:0.75 to obtain the liquid maltitol with a maltitol content of 50.2% and a sorbitol content of 5.7%.

* * * * *